United States Patent
Starosta et al.

(10) Patent No.: US 7,531,084 B2
(45) Date of Patent: May 12, 2009

(54) REACTOR FOR THERMALLY CRACKING MONOFUNCTIONAL AND POLYFUNCTIONAL CARBAMATES

(75) Inventors: Dieter Starosta, Schwarzheide (DE); Peter Pfab, Schwarzheide (DE); Volker Krase, Lauchhammer (DE); Andreas Schmidt, Schwarzheide (DE); Matthias Kloetzer, Kroppen (DE); Andreas Otterbach, Tervuren (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 312 days.

(21) Appl. No.: 10/508,710

(22) PCT Filed: Apr. 9, 2003

(86) PCT No.: PCT/EP03/03672

§ 371 (c)(1),
(2), (4) Date: Sep. 30, 2004

(87) PCT Pub. No.: WO03/084921

PCT Pub. Date: Oct. 16, 2003

(65) Prior Publication Data

US 2005/0203311 A1  Sep. 15, 2005

(30) Foreign Application Priority Data

Apr. 10, 2002 (DE) .............................. 102 15 778

(51) Int. Cl.
*C10G 9/14* (2006.01)
*C10G 9/00* (2006.01)
*B01J 19/00* (2006.01)
*F28D 15/00* (2006.01)

(52) U.S. Cl. ..................... 208/132; 208/106; 422/138; 422/139; 422/198; 165/104.11; 165/104.12

(58) Field of Classification Search ................ 48/127.5, 48/180.1, 189.1; 110/187, 196, 201; 208/106, 208/80, 132, 160, 153; 165/58, 60, 66, 104.11, 165/104.12, 104.04, 104.13, 104.18, 104.2, 165/158; 392/302, 303, 309; 261/146, 148, 261/151, 152, 158, 16, 28, 108; 159/22; 122/208, 412, 488, 491; 429/120; 422/138, 422/139, 155, 158, 173, 188, 198; 560/345
See application file for complete search history.

(56) References Cited

U.S. PATENT DOCUMENTS 2,692,275 A  10/1954  Bortnick (Continued)

FOREIGN PATENT DOCUMENTS

DE  26 35 490  2/1977

(Continued)

*Primary Examiner*—Walter D Griffin
*Assistant Examiner*—Huy-Tram Nguyen
(74) *Attorney, Agent, or Firm*—Oblon, Spivak, McClelland, Maier & Neustadt, P.C.

(57) ABSTRACT

A reactor for the thermal cleavage of monofunctional and/or polyfunctional carbamic esters into the corresponding isocyanate and hydroxyl components in the liquid phase having devices for introduction of heat into the reactor, where the devices are heat exchanger plates through which a heat transfer medium flows and have a geometry defined by the ratio of the degassing area to the volume and arrangement of the heating surfaces which makes it possible for the cleavage to be carried out in a two-phase mixture which has a gas content of over 50% by volume.

15 Claims, 1 Drawing Sheet

U.S. PATENT DOCUMENTS

| | | | | |
|---|---|---|---|---|
| 3,400,758 | A | * 9/1968 | Lee | 165/159 |
| 3,630,276 | A | * 12/1971 | Paine et al. | 165/158 |
| 3,744,272 | A | * 7/1973 | Oldberg | 62/439 |
| 4,294,774 | A | 10/1981 | Henson et al. | |
| 4,700,771 | A | * 10/1987 | Bennett et al. | 165/133 |
| 5,087,739 | A | * 2/1992 | Bohmholdt et al. | 560/345 |
| 5,616,784 | A | * 4/1997 | Schwarz et al. | 560/345 |
| 6,478,077 | B1 | * 11/2002 | Story et al. | 165/104.12 |
| 7,179,935 | B2 | * 2/2007 | Stroefer et al. | 560/345 |

FOREIGN PATENT DOCUMENTS

| | | | |
|---|---|---|---|
| DE | 100 32 302 A 1 | * | 10/2001 |
| EP | 0 092 738 | | 11/1983 |
| EP | 0 524 554 | | 1/1993 |
| WO | WO 01/51448 A2 | * | 1/2001 |

* cited by examiner

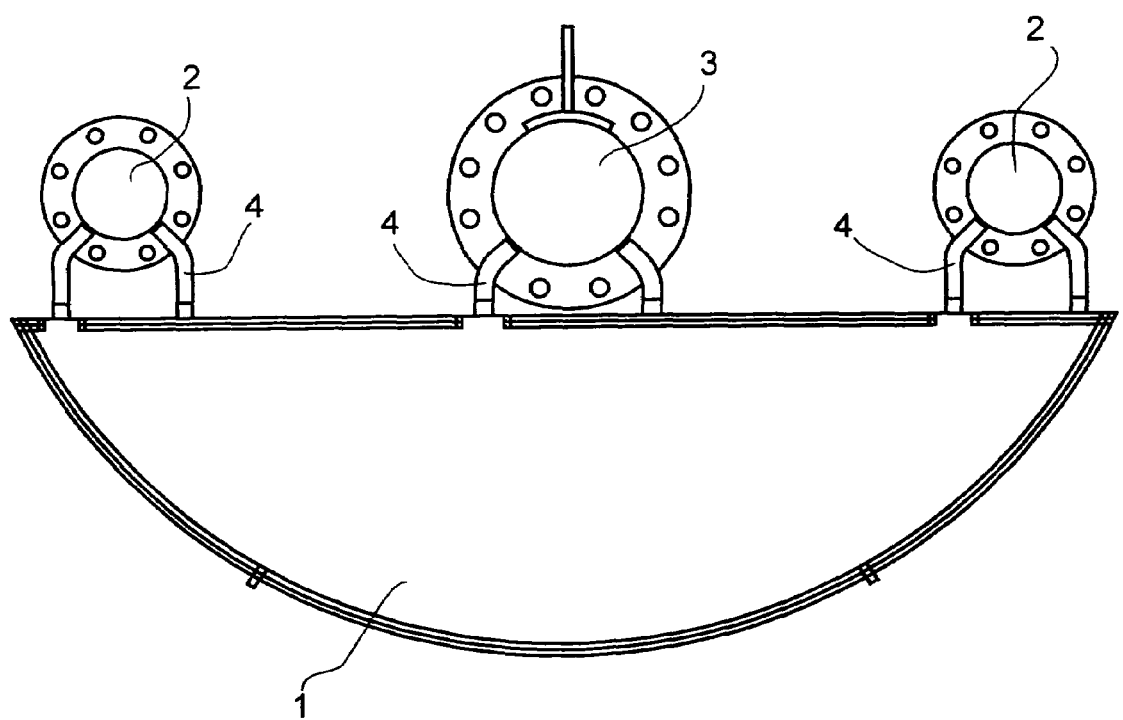

REACTOR FOR THERMALLY CRACKING MONOFUNCTIONAL AND POLYFUNCTIONAL CARBAMATES

The invention relates to a reactor for the thermal cleavage of monofunctional and/or polyfunctional carbamic esters in the liquid phase and to a process for the thermal cleavage of carbamic esters in a reactor.

The thermal cleavage of carbamic esters to obtain isocyanates has been known for a long time. A problem in this process is that the cleavage is reversible, i.e. the isocyanate component and hydroxyl component formed as cleavage products recombine when the hot reaction mixtures are cooled. To prevent the reverse reaction, it is necessary for the isocyanate and hydroxyl components to be separated off from the reaction mixture immediately by means of suitable process engineering measures.

A further problem in the thermal cleavage of carbamic esters is the loss of starting material due to many irreversible decomposition reactions of the carbamic esters. For this reason, processes have been developed to suppress these, in particular by reducing the reaction temperature by the use of catalysts. Basic catalysts as described, for example, in U.S. Pat. No. 2,692,275 are suitable, but they also catalyze the decomposition reactions. The aluminum, zinc and tin compounds described in DE-B 26 35 490 are to be more selective and preferentially accelerate the cleavage reaction.

A further process improvement which has been proposed, in particular for the preparation of polyfunctional isocyanates in the case of which there is an increased risk of polymerization and residue formation, is dilution of the carbamic esters with inert solvents or introduction of inert solvents into the cleavage reactor, for example as described in EP-A 0 092 738. These measures enable fouling of the surfaces in the reactor to be reduced and by-products can be discharged. Disadvantages of such an addition of auxiliaries are the resulting increased process engineering outlay and the costs of the auxiliary consumed.

The use of catalytically active solvents, for example dialkylanilines as proposed in U.S. Pat. No. 4,294,774, is also known.

Many proposals for the configuration of the cleavage reactor are known. The cleavage reactors have to take into account the above-described particular aspects of the carbamic ester cleavage reaction, in particular the recombination of the cleavage products, and also suppress secondary reactors. For this purpose, it is necessary to keep the residence time of the carbamic esters in the hot zone of the cleavage reactor very short and to remove the cleavage products quickly from the reaction zone. EP-A 0 092 738 describes thin film evaporators and falling film evaporators as cleavage reactors suitable for this purpose. However, such reactors are expensive for use on a large industrial scale and the thin film evaporators have the additional disadvantage that they have to be provided with a stirrer, i.e. they have moving parts. The greatest disadvantage of such reactors is that in the case of the cleavage of polyfunctional carbamic esters they become fouled by polymerization if they are operated for a period longer than a few days, so that economical operation is not possible.

EP-A 0 524 554 describes the use of simple vessels containing internals for introduction of the heat of reaction as cleavage reactors. The geometry of the reactor, characterized by the ratio of the degassing area to the volume and by the arrangement of the heating surfaces, makes it possible for the cleavage to be carried out in a two-phase mixture which has a gas content of over 50% by volume. In these reactors, the reaction medium is present in a boiling-like state in which the gases resulting from the cleavage reaction and starting material vapors ascend through the liquid.

Examples which may be mentioned are: Robert evaporators, Herbert evaporators with and without forced circulation, "heating plug vaporizers" having vertical, oblique or horizontal heating plugs, Caddle-type evaporators, tanks with tightly coiled heating coils, and similar reactors which have a high heat input into a small volume.

When the boundary conditions described are adhered to, such reactors can be operated so that polyfunctional carbamic esters can be cleaved to form the corresponding isocyanate and hydroxyl components without the reactors having to be shut down and cleaned during the course of continuous operation for a number of weeks.

The frequently employed variant of a shell-and-tube reactor with the heat transfer medium being passed through the tubes and the reaction medium being passed through the intermediate space between the tubes of the tube bundle suffers from the problem that thermal stresses occur in the region of the weld for fixing the tubes in tube plates at both ends of the reactor and affect the sealing surfaces, resulting in leaks during start-up and shutdown and in caked product being formed in this region of the reactor.

It is an object of the present invention to provide a reactor which has devices for introduction of heat of reaction and displays increased operating times of a number of months and can be constructed simply and inexpensively and be extended in a simple manner if required, and does not have the disadvantages indicated above.

The achievement of this object starts out from a reactor for the thermal cleavage of monofunctional and/or polyfunctional carbamic esters into the corresponding isocyanate and hydroxyl components in the liquid phase having devices for introduction of heat into the reactor whose geometry, defined by the ratio of the degassing area to the volume of the liquid phase and the arrangement of the heating surfaces, makes it possible for the cleavage to be carried out in a two-phase mixture having a gas content of over 50% by volume.

In the reactor of the present invention, the devices are heat exchanger plates through which a heat transfer medium flows.

The reactor of the present invention is operated under process conditions as described in EP-A 0524 554. The reactor is operated in such a way that the two-phase mixture of boiling liquid and vapor phase comprising vaporized starting material and the cleavage gases contains a proportion of over 50% by volume of gas.

The volume-based gas content of the two-phase mixture is preferably from 50 to 98%, more preferably from 60 to 96% and particularly preferably from 75 to 90%.

To achieve such high gas contents in the two-phase mixture, it is useful for the reactors to meet particular geometric requirements.

For example, it is useful for the height of the reaction zone in the reactor to be not less than 0.2 m and not greater than 2 m so as to promote the formation of the gas-rich two-phase mixture. The degassing area of the reactor, i.e. the free surface of the liquid at which the gas can escape, should be such that the gas velocity at the upper end of the reaction zone is not less than 1 m/s and not more than 30 m/s, preferably in the range from 2 m/s to 20 m/s. The heat transfer surfaces should have dimensions such that the temperature difference between heating medium and reaction medium is less than 40° C., but at the same time the quantity of heat necessary for the strongly endothermic reaction can be introduced into the volume which has been restricted by residence time requirements.

The reactors are operated fully continuously, both in respect of the feed and in respect of taking off liquid in order to avoid accumulation of relatively high-boiling by-products. The conversion per path through the reactor is in the range from 30 to 95%, preferably from 60 to 90%, conversion of urethane in the reactor feed into isocyanate taken off.

The mean residence times are from 1 to 80 minutes, preferably from 5 to 60 minutes, and are defined as the quotient of the liquid contents of the reactor under reaction conditions and the reactor contents taken in liquid form from the reactor per minute.

The reaction is carried out without any addition of solvent or diluent and without an inert gas being conveyed through the reactor.

The feed to the reactor is a product mixture which comprises the carbamic ester and by-products formed in a circulation process in which a carbamic ester is prepared from an amine with addition of urea and a hydroxyl component and this is then cleaved to form the isocyanate, with part of the contents of the reactor being taken from the reactor and recirculated to the first stage of the process. Such by-products can be, inter alia, high molecular weight products, preferably isocyanurate. Surprisingly, it is sufficient for the carbamic ester content of the feed to the reactor to be from 80 to 90%. A higher purity of the carbamic ester makes operation of the cleavage reactor easier, since fouling problems then become less significant. It is also possible to use reactor feeds containing less than 80% of carbamic ester, but fouling problems then increase, particularly when polyfunctional carbamic esters are being cleaved. The feed to the cleavage reactor can, if desired, further comprise the catalyst necessary for the cleavage.

An important aspect of the invention is the fact that the carbamic ester does not have to be completely vaporized and condensed again to free it of oligomeric by-products before it is fed into the reactor, as described in EP-A 355 433, but instead a certain level of by-products in the reactor can be tolerated.

The use according to the present invention of heat exchanger plates as devices for the introduction of heat makes it possible to cleave even carbamic esters having a relatively high level of impurities and a carbamic ester content of from 70 to 85%.

According to the present invention, heat exchanger plates are used as devices for introduction of heat in the cleavage reactor.

Heat exchanger plates are devices known in process engineering for heat transfer. They are generally made up of two essentially parallel metal sheets which are joined to one another, in particular welded together, and form an interior space through which a heat transfer medium can be passed via suitable inlet and outlet lines. To increase the stability, in particular the compressive strength, the plates are frequently welded together at a point and/or along lines in a plurality of places.

Heat exchanger plates are generally used in a stack, i.e. as a plurality of parallel heat exchanger plates. For use in the reactor of the present invention, the heat exchanger plates are preferably made of stainless steel, in particular a stainless steel having the material numbers 1.45xx, with the two "x"s being able to denote any numbers, preferably a stainless steel having one of the material numbers 1.4571, 1.4529, 1.4401, 1.4404 or 1.4462. The heat exchanger plates are preferably provided with a smooth, in particular polished, for example electropolished, surface.

Due to their geometric shape, the heat exchanger plates force the reaction mixture flowing in the intermediate spaces between the heat exchanger plates to flow in the longitudinal direction. As a result, heat transfer between the reaction mixture and the heat transfer medium flowing through the heat exchanger plates is poorer than in the case of a shell-and-tube reactor in which transverse mixing of the reaction medium is also possible between the tubes through which heat transfer medium flows. For this reason, as a given reaction volume, a cleavage reactor provided with heat exchanger plates requires a larger heat transfer area than does a shell-and-tube cleavage reactor. Thus, for example, a heat transfer area of 150 $m^2$ for a shell-and-tube reactor has to be increased to 228 $m^2$ for a reactor provided with heat exchanger plates at the same reaction volume. However, since the plate reactor is simpler to manufacture, the manufacturing costs are nevertheless only 25-30% of the manufacturing costs for the shell-and-tube reactor.

Furthermore, when heat exchanger plates are used, the temperature at which the heat transfer medium is introduced and thus the stress on the heating surfaces can be reduced, frequently by up to about 20° C., for a given reaction volume because of the increased heat transfer area. This leads to reduced deposit formation on the surfaces and thus to a lengthening of the uninterrupted operating time of the reactor, frequently by about 20%.

The cleavage reactor of the present invention is preferably configured so that the heat exchanger plates dip partly or completely into the liquid phase and the two-phase reaction mixture.

As heat transfer medium in the heat exchanger plates, preference is given to using high-boiling liquids, i.e. liquids having a boiling point which is at least about 40° C. above the cleavage temperature of the carbamic ester used, in particular a boiling point in the range from 280 to 400° C., preferably from 350 to 390° C. Particularly preferred heat transfer media are a Marlotherm® fluid or mixtures of Marlotherm® fluids. Marlotherms® are mixtures of dibenzyltoluenes (Marlotherm®S) or mixtures of isomeric benzyltoluenes (Marlotherm® L).

The heat exchanger plates preferably have dimensions such that the ratio of the total heat transfer area of the heat exchanger plates to the total volume of the liquid phase in the reactor is in the range from 10 to 320 $m^2/m^3$, preferably in the range from 20 to 150 $m^2/m^3$, in particular in the range from 50 to 80 $m^2/m^3$.

In a preferred embodiment, the cleavage reactor is a horizontal cylinder in which the heat exchanger plates are configured as segments of a circle which are arranged parallel to one another and perpendicular to the longitudinal direction of the reactor in the lower half of the reactor.

The segments of a circle are particularly preferably smaller than half the cross section of the reactor.

The supports holding the heat exchanger plates are preferably made as vibration-free as possible so as not to interfere with the turbulence in the reactor. For this purpose, the heat exchanger plates are preferably attached to inlet and outlet pipes arranged in the longitudinal direction of the reactor above the heat exchanger plates by means of curved pipe sections.

As a result of this particular configuration of the inlet and outlet for the heat transfer medium, there are no longer any large, heated areas at which caking of by-products could take place in the caps at the two ends of the cleavage reactor in the region of the inlet or outlet of the heat transfer medium, as is the case on the heated tube plates of shell-and-tube reactors.

Furthermore, the cleavage reactor of the present invention which has heat exchanger plates can readily be adapted to a need for an increased heat transfer area by installation of additional heating plates and enlargement of the outer wall of the reactor.

The present invention also provides a process for the thermal cleavage of carbamic esters in a cleavage reactor as described above.

The monofunctional or polyfunctional carbamic esters which can be used are in principle subject to no restrictions.

Likewise, the process is not restricted in respect of the further work-up of the cleavage gases leaving the reactor during the cleavage reaction. These are preferably fractionated by rectification, as described in EP-A 0 524 554.

The process is preferably carried out with no solvent being added to the reaction medium.

The cleavage rector is preferably operated at a pressure of from 2 to 200 mbar, particularly preferably at a pressure of from 5 to 100 mbar.

The cleavage reactor is preferably operated so that the velocity of the gases leaving the two-phase reaction medium at the upper end of the reaction zone is from 1 to 30 m/s, preferably from 2 to 20 m/s, when the reaction is carried out at an absolute pressure in the range from 2 mbar and 200 mbar.

The invention is illustrated below with the aid of a drawing and an example.

FIG. 1 schematically shows a preferred embodiment of a heat exchanger plate in cross section.

FIG. 1 shows a heat exchanger plate 1 having the shape of a circle. The upper part of the heat exchanger plate 1 is provided with distribution and collection manifolds 2, 3 for the heat transfer medium, which are, by way of example, configured as tubes having a circular cross-section. In the preferred variant shown in FIG. 1, the heat transfer medium is fed in via the outer distribution and collection manifold 2 and discharged via the inner distribution and collection manifold 3. The distribution and collection manifolds 2, 3 are connected to the heat exchanger plate 1 by means of curved pipe sections 4 which ensure that the heat exchanger plates 1 are held in place in a virtually vibration-free manner. In the cleavage reactor of the present invention, a plurality of heat exchanger plates 1 are arranged one after the other with corresponding distribution and collection manifolds 2, 3 and curved pipe sections 4. The curved pipe sections arranged one after the other can therefore be referred to as a comb-like support for the heat exchanger plates 1.

A liquid feed stream of 45 kg/h of hexamethylenedi-n-butylurethane was fed continuously into a horizontal cylindrical reactor having a diameter of 40 cm. The cleavage reaction was carried out at 240° C. in the reaction medium and a pressure of 30 mbar. A liquid stream of 15 kg/h was taken off continuously from the bottom of the reactor by means of a pump. The liquid holdup in the reactor and the pipes was about 10 liters. The mean residence time was in the range from 30 to 40 minutes. About 10 kW of thermal power had to be introduced into the reaction medium to maintain the endothermic reaction and to vaporize the reaction products. Marlotherm® S was used as heat transfer medium.

Under the abovementioned conditions, a comparison was made between a shell-and-tube cleavage reactor containing 15 tubes each having a diameter of 1.8 cm and a cleavage reactor according to the present invention provided with heat exchanger plates. In the comparative experiment using the shell-and-tube reactor, the inlet temperature of the Marlotherm® fluid was 260° C. and the heat exchange area was about 0.35 $m^2$.

In comparison, the reactor according to the present invention was provided with 9 heat exchanger plates which were arranged vertically in the reactor with a spacing between the individual plates of 15 mm. The inlet temperature of the Marlotherm® fluid was 258° C. and the heat exchange area was about 0.6 $m^2$.

The cleavage of the carbamic ester occurred at the same conversion of about 95% both in the reactor of the prior art and in the reactor according to the present invention. However, chromatographic analysis showed that the increase in high molecular weight compounds which lead to fouling, in particular allophanates, cyanurates, etc., was about 15% lower when using the cleavage reactor of the present invention provided with heat exchanger plates. After an operating time of three weeks, no fouling on the heat exchanger surfaces was found in the case of the reactor according to the present invention, in contrast to the reactor of the prior art.

We claim:

1. A reactor comprising devices for introduction of heat into the reactor,
   wherein the devices are heat exchanger plates wherein a heat transfer medium flows through said heat exchanger plates,
   said reactor is capable of carrying out a thermal cleavage of monofunctional and/or polyfunctional carbamic esters into the corresponding isocyanate and hydroxyl components in a liquid phase without addition of a solvent,
   and the reactor is capable of carrying out said cleavage in a two-phase mixture comprising a gas content of over 50% by volume due to the geometry of said reactor, wherein the geometry is defined by the ratio of the degassing area to the volume of the liquid phase and the arrangement of the heating surfaces,
   wherein the heat exchanger plates are configured as segments of a circle arranged parallel to one another and perpendicular to the longitudinal axis of the reactor in the lower half of the reactor, and
   wherein the heat exchanger plates are supported by curved pipe sections in a largely vibration-free manner along feed and distribution pipes arranged in the longitudinal direction of the reactor above the heat exchanger plates.

2. The reactor as claimed in claim 1, wherein the heat exchanger plates dip partly or completely into the liquid phase.

3. The reactor as claimed in claim 1, wherein the heat transfer medium is a high-boiling liquid.

4. The reactor as claimed in claim 3, wherein the high-boiling liquid is a mixture of dibenzyltoluenes, mixture of isomeric benzyltoluenes, or mixtures thereof.

5. The reactor as claimed in claim 1, wherein the ratio of the total heat transfer area of the heat exchanger plates to the total volume of the liquid phase in the reactor is in the range from 10 to 320 $m^2/m^3$.

6. The reactor as claimed in claim 5, wherein the ratio of the total heat transfer area of the heat exchanger plates to the total volume of the liquid phase in the reactor is in the range from 20 to 150 $m^2/m^3$.

7. The reactor as claimed in claim 6, wherein the ratio of the total heat transfer area of the heat exchanger plates to the total volume of the liquid phase in the reactor is in the range from 20 to 80 $m^2/m^3$.

8. The reactor as claimed in claim 1, wherein the reactor is configured as a horizontal cylinder.

9. The reactor as claimed in claim 8, wherein the segments of a circle are smaller than half the cross section of the reactor.

10. The reactor as claimed in claim 9, wherein the segments of a circle have an area of from 20 to 30% of the cross-sectional area of the reactor.

11. A process for producing isocyanate and hydroxyl components, the process comprising:
   thermally cleaving monofunctional and/or polyfunctional carbamic esters into the corresponding isocyanate and hydroxyl components in the liquid phase without addition of a solvent in a two-phase in a reactor
   wherein said reactor comprises devices for introduction of heat into the reactor,
   the devices are heat exchanger plates wherein a heat transfer medium flows through said heat exchanger plates, and
   the reactor is capable of carrying out said cleaving in a two-phase mixture comprising a gas content of over 50% by volume due to the geometry of said reactor, wherein the geometry is defined by the ratio of the degassing area to the volume of the liquid phase and the arrangement of the heating surfaces,
   wherein the heat exchanger plates are configured as segments of a circle arranged parallel to one another and perpendicular to the longitudinal axis of the reactor in the lower half of the reactor, and
   wherein the heat exchanger plates are supported by curved pipe sections in a largely vibration-free manner along feed and distribution pipes arranged in the longitudinal direction of the reactor above the heat exchanger plates.

12. The process as claimed in claim 11, wherein the process is carried out at a pressure of from 2 to 200 mbar in the reactor.

13. The process as claimed in claim 11, wherein the process is carried out at a pressure of from 5 to 100 mbar in the reactor.

14. The process as claimed in claim 11, wherein the velocity of the gases leaving the two-phase mixture at the upper end of the reaction zone is from 1 m/s to 30 m/s.

15. The process as claimed in claim 14, wherein the velocity of the gases leaving the two-phase mixture at the upper end of the reaction zone is from 2 m/s to 20 m/s.

* * * * *